United States Patent [19]
Stone

[11] Patent Number: 5,637,497
[45] Date of Patent: Jun. 10, 1997

[54] APPARATUS AND METHOD FOR CLEANING AND DISINFECTING CONTACT LENSES

[75] Inventor: Ralph P. Stone, Arlington, Tex.

[73] Assignee: Alcon Laboratories, Inc., Fort Worth, Tex.

[21] Appl. No.: 496,241

[22] Filed: Jun. 28, 1995

[51] Int. Cl.$^6$ .................................. C12P 1/00; A61L 2/18
[52] U.S. Cl. ................ 435/264; 435/177; 435/180; 435/181; 422/30; 424/661
[58] Field of Search ........................... 435/264, 181, 435/177, 180; 422/30; 424/661

[56] References Cited

U.S. PATENT DOCUMENTS

| | | | |
|---|---|---|---|
| 4,855,234 | 8/1989 | Hendrickson et al. | 435/181 |
| 5,011,661 | 4/1991 | Schafer et al. | 422/30 |
| 5,338,480 | 8/1994 | Dziabo et al. | 252/187.21 |
| 5,531,963 | 7/1996 | Powell, Jr. | 422/30 |

FOREIGN PATENT DOCUMENTS 3286158  11/1988  Japan .................. 435/264

*Primary Examiner*—Helen Pratt
*Attorney, Agent, or Firm*—Jeffrey S. Schira

[57] ABSTRACT

A lens storage container having an interior coated with an enzymatic cleaning composition useful for cleaning and disinfecting contact lenses.

21 Claims, 1 Drawing Sheet

APPARATUS AND METHOD FOR CLEANING AND DISINFECTING CONTACT LENSES

BACKGROUND OF THE INVENTION

The present invention relates to a method of storing contact lenses and more particularly to a method for cleaning and disinfecting contact lenses.

Numerous methods have been previously described for cleaning and disinfecting contact lenses. Prior art cleaning methods include the use of surfactant and/or proteolytic enzymes. Prior art disinfection methods include the use of heat and/or chemical agents such as hydrogen peroxide, polymeric biguanides, polymeric quaternary ammonium compounds, thimerosal, and benzalkonium chloride. The prior art also describes the simultaneous cleaning and disinfecting of contact lenses by contacting the lens in an aqueous medium containing both an enzyme, and an antimicrobial agent.

The commercially available prior art enzyme/disinfectant combinations use a solid enzymatic cleaning composition, usually packaged separately from the aqueous disinfectant and in tablet form. In use, the tablet must be placed in a vial and dissolved in the disinfectant. This cumbersome, multi-step procedure compromises patient compliance and as a result, surveys have shown that less than half of the contact lenses wearers enzymatically clean his or her contact lenses on a regular basis.

Accordingly, a need continues to exist for a simple and convenient method for cleaning and disinfecting contact lenses.

BRIEF DESCRIPTION OF THE INVENTION

The present invention includes a disposable lens storage container having an interior coating of an enzymatic cleaning composition. Coating the interior of the container removes the need to have a separate enzyme tablet and greatly simplifies the enzymatic cleaning and chemical disinfection of contact lenses.

Accordingly, one objective of the present invention is to provide a contact lenses storage container having an interior coated with an enzymatic cleaning composition.

Another objective of the present invention is to provide a simplified method for enzymatically cleaning and chemically disinfecting contact lenses.

These and other objectives and advantages of the present invention will become apparent from the detailed description and claims which follow.

DETAILED DESCRIPTION OF THE INVENTION

Figure 1:
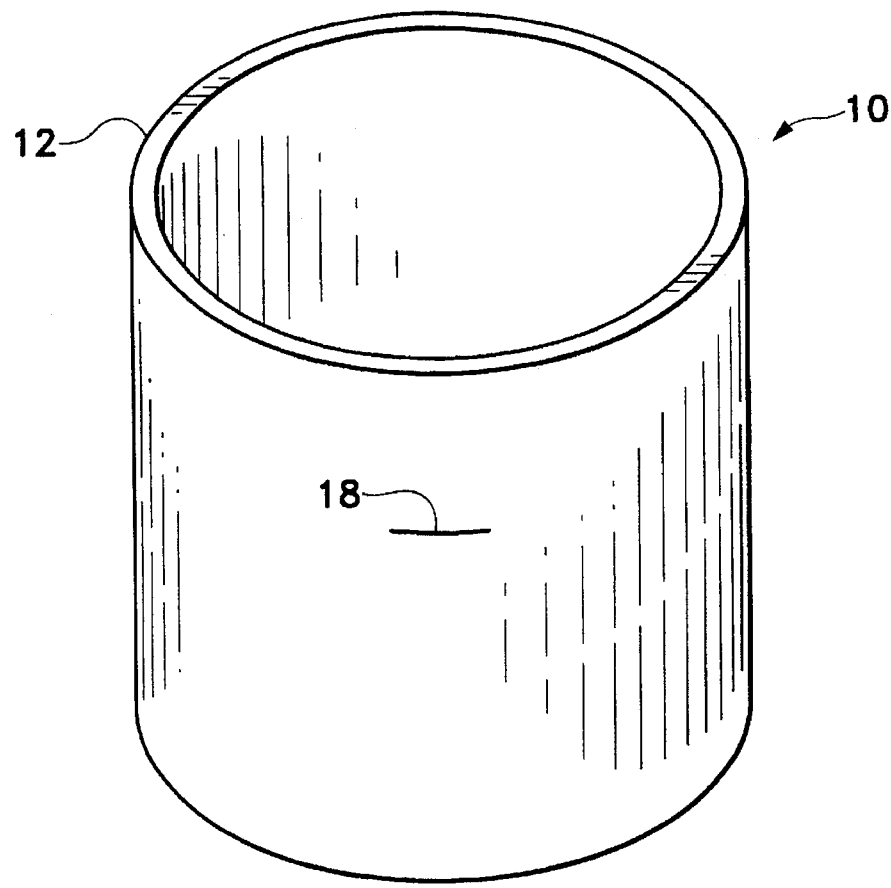
FIG. 1 is a perspective view of one embodiment of the present invention.
Figure 2:
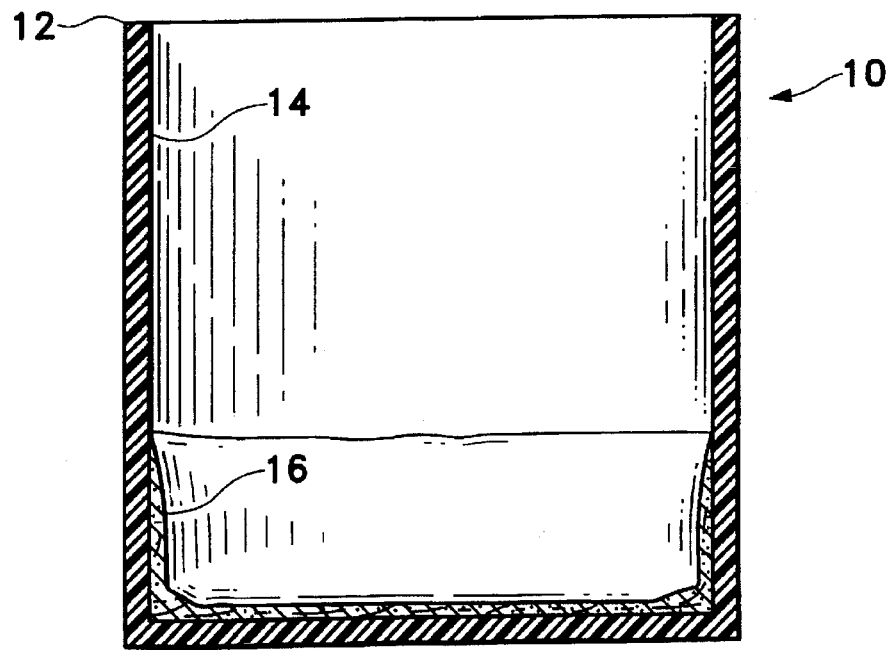
FIG. 2 is a cross-section view of the device illustrated in FIG. 1.

The device 10 of the present invention generally comprises a container 12 having interior surface 14 coated with an enzymatic cleaning composition 16. Container 12 may contain gradation mark 18 indicating an appropriate fill level (e.g. 5 or 10 milliliters). Container 12 preferably is transparent and may be made from any of a variety of plastic materials well-known in the art.

Coating 16 preferably contains an enzyme such as amylases, lipases or proteases (e.g. pancreatin, trypsin, subtilisin, collagenase, keratinase, carboxylase, papain, bromelain, aminopeptidase, Aspergillo peptidase, pronase E or dispase), but any enzyme useful in removing deposits from contact lenses may be used. The amount of coating 16 should be adjusted to provide sufficient enzymatic activity to clean the contact lens when container 12 is filled with an aqueous disinfecting solution. Coating 16 may contain tonicity adjusting or buffering agents such as sodium and potassium chloride, dextrose and/or calcium and magnesium chloride, chelating agents such as ethylenediaminetetraacetic acid (EDTA) and its salts and/or a surfactant such as polyethylene glycol esters of fatty acids, polyoxypropylene esters or polyoxypropylene block copolymers of ethylene diamine.

Coating 16 may be applied to container 12 in a variety of ways. For example, a solution containing a level of pancreatin or subtilisin to yield approximately 2000 activity units in the final solution and around 1.0% polyethylene glycol 8000 may be added to container 12 and allowed to dry to form coating 16 over the bottom and lower sides of container 12. Alternatively, a solution containing pancreatin or subtilisin and a pluronic or tetronic surfactant (e.g. pluronic F127) may be added to container 12 and allowed to dry to form coating 16 over the bottom and lower sides of container 12. Additionally, a solution containing 2% of a water soluble acrylate polymer and pancreatin or subtilisin may be added to container 12 and allowed to dry to form coating 16 over the bottom and lower sides of container 12. An acrylate polymer may also be used that allows the disinfecting solution to diffuse into and out of coating 16. In addition, a solution containing pancreatin or subtilisin and ethyl vinyl acetate may be added to container 12 and allowed to dry to form coating 16 over the bottom and lower sides of container 12. Finally, coating 16 may also be formed from a soluble polymer that allows the enzyme to diffuse slowly into the disinfecting solution so that only the enzyme and no excipients is released into the solution.

In use, container 12 is filled to gradation 18 with a suitable aqueous disinfecting solution, preferably containing an oxidative antimicrobial agent or a non-oxidative polymeric antimicrobial agent. Suitable antimicrobial agents include hydrogen peroxide or peroxy compounds, polymeric quaternary ammonium compounds, biguanides, benzalkonium halides, salts of alexidine, alexidine free base, salts of chlorhexidine and hexamathylene biguanides and their polymers. Suitable solutions are commercially available from Alcon Laboratories, Fort Worth, Tex. under the trademark OPTI-FREE® and OPTI-ONE®, Allergan, Irvine, Calif. under the trademark COMPLETE® and Bausch & Lomb, Rochester, N.Y. under the trademark RENU®. The disinfecting solution dissolves coating 16 to form an aqueous enzymatic cleaning/disinfecting solution. The contact lenses are placed within the cleaning/disinfecting solution held in container 12 for a time sufficient to clean and disinfect the lenses, for example, between 15 minutes and overnight, preferably between about 4 hours and 8 hours. After the lenses are cleaned and disinfected, container 12 may be discarded or, if the coating is formulated to release the enzyme slowly, container 12 may be reused.

This description is given for purposes of illustration and explanation. It will be apparent to those skilled in the relevant art that changes and modifications may be made to the invention described above without departing from its scope or spirit.

I claim:

1. A method of cleaning and disinfecting a contact lens, comprising the steps of:
   a) providing a lens storage container with an interior surface coated with a cleaning composition containing an enzyme;
   b) at least partially filling the interior with a lens disinfecting solution so as to at least partially dissolve the cleaning composition, thereby forming an aqueous cleaning and disinfecting solution;
   c) inserting the contact lens into the aqueous cleaning and disinfecting solution; and
   d) soaking the contact lens in the aqueous cleaning and disinfecting solution for an amount of time sufficient to clean and disinfect the contact lens.

2. The method of claim 1 wherein the enzyme comprises a proteolytic enzyme.

3. The method of claim 2 wherein the proteolytic enzyme comprises pancreatin, trypsin, subtilisin, collagenase, keratinase, carboxylase, papain, bromelain, aminopeptidase, Aspergillo peptidase, pronase E or dispase.

4. The method of claim 3 wherein only the proteolytic enzyme is dissolved in the disinfecting solution.

5. The method of claim 1 wherein the lens disinfecting solution comprises polymeric quaternary ammonium compounds, biguanides, benzalkonium halides, salts of alexidine, alexidine free base, salts of chlorhexidine and hexamathylene biguanides and their polymers.

6. The method of claim 1 wherein the cleaning composition further comprises a surfactant.

7. The method of claim 1 wherein the cleaning composition further comprises a tonicity adjusting agent.

8. The method of claim 1 wherein the cleaning composition further comprises a buffering agent.

9. A method of cleaning and disinfecting a contact lens, comprising the steps of:
   a) providing a lens storage container with an interior surface coated with a proteolytic enzyme cleaning composition;
   b) at least partially filling the interior with a lens disinfecting solution containing a non-oxidative polymeric antimicrobial agent so as to dissolve the enzyme cleaning composition, thereby forming an aqueous cleaning and disinfecting solution;
   c) inserting the contact lens into the aqueous cleaning and disinfecting solution; and
   d) soaking the contact lens in the aqueous cleaning and disinfecting solution for an amount of time sufficient to clean and disinfect the contact lens.

10. The method of claim 9 wherein the proteolytic enzyme comprises pancreatin, trypsin, subtilisin, collagenase, keratinase, carboxylase, papain, bromelain, aminopeptidase, Aspergillo peptidase, pronase E or dispase.

11. The method of claim 9 wherein the non-oxidative polymeric antimicrobial agent comprises polymeric quaternary ammonium compounds, biguanides, benzalkonium halides, salts of alexidine, alexidine free base, salts of chlorhexidine and hexamathylene biguanides and their polymers.

12. The method of claim 9 wherein the enzymatic cleaning composition further comprises a surfactant.

13. The method of claim 9 wherein the enzymatic cleaning composition further comprises a tonicity adjusting agent.

14. The method of claim 9 wherein the enzymatic cleaning composition further comprises a buffering agent.

15. A method of cleaning and disinfecting a contact lens, comprising the steps of:
   a) providing a lens storage container with an interior surface coated with a proteolytic enzyme cleaning composition;
   b) at least partially filling the interior with a lens disinfecting solution containing an oxidative antimicrobial agent so as to dissolve the enzyme cleaning composition, thereby forming an aqueous cleaning and disinfecting solution;
   c) inserting the contact lens into the aqueous cleaning and disinfecting solution; and
   d) soaking the contact lens in the aqueous cleaning and disinfecting solution for an amount of time sufficient to clean and disinfect the contact lens.

16. The method of claim 15 wherein the proteolytic enzyme comprises pancreatin, trypsin, subtilisin, collagenase, keratinase, carboxylase, papain, bromelain, aminopeptidase, Aspergillo peptidase, pronase E or dispase.

17. The method of claim 15 wherein the enzymatic cleaning composition further comprises a surfactant.

18. The method of claim 15 wherein the enzymatic cleaning composition further comprises a tonicity adjusting agent.

19. The method of claim 15 wherein the enzymatic cleaning composition further comprises a buffering agent.

20. An apparatus for cleaning and disinfecting contact lenses comprising:
   a lens storage container with an interior surface coated with a proteolytic enzyme cleaning composition.

21. The apparatus of claim 20, wherein the proteolytic enzyme comprises pancreatin, trypsin, subtilisin, collagenase, keratinase, carboxylase, papain, bromelain, aminopeptidase, Aspergillo peptidase, pronase E or dispase.

* * * * *